United States Patent [19]

Taniuchi et al.

[11] Patent Number: 5,076,828
[45] Date of Patent: Dec. 31, 1991

[54] OXYALKYLATED QUATERNARY AMMONIUM COMPOUNDS AND PLANT GROWTH REGULATING COMPOSITIONS CONTAINING SAID COMPOUNDS

[75] Inventors: Akira Taniuchi, Kyoto; Hironori Kataoka, Nara, both of Japan

[73] Assignee: Dai-Ichi Kogyc Seiyaku Co., Ltd., Kyoto, Japan

[21] Appl. No.: 439,080

[22] Filed: Nov. 20, 1989

[30] Foreign Application Priority Data

| Nov. 28, 1988 | [JP] | Japan | 63-301475 |
| Nov. 28, 1988 | [JP] | Japan | 63-301476 |
| Nov. 28, 1988 | [JP] | Japan | 63-301477 |
| Mar. 30, 1989 | [JP] | Japan | 1-80894 |
| Aug. 21, 1989 | [JP] | Japan | 1-214634 |

[51] Int. Cl.$^5$ .............................. A01N 33/12
[52] U.S. Cl. .......................... 71/86; 71/95; 71/96; 71/98; 71/103; 71/106; 71/113; 71/114; 71/115; 564/281; 564/285; 564/294
[58] Field of Search ............ 564/281, 285, 294; 71/86, 95, 96, 98, 103, 106, 113, 114, 115

[56] References Cited

PUBLICATIONS

Mannheimer, H. S., Chem. Abstracts, vol. 77, No. 8; 50546t (1972).
Tanuichi et al., Chem. Abstracts, vol. 109, No. 9, 73006k (1988).
Yamamoto, T., Chem. Abstracts, vol. 106, No. 22; 178069z (1987).

*Primary Examiner*—Johann Richter
*Attorney, Agent, or Firm*—Jordan and Hamburg

[57] ABSTRACT

This invention relates to novel oxyalkylated quaternary ammonium compounds, processes for their production and plant growth regulating compositions containing the same compounds. Each of these oxyalkylated quaternary ammonium compounds consists of an oxyalkylated quaternary ammonium cation and an anion selected from among carboxylic acid residues, aminosulfonic acid residues and phosphoric acid ester residues. These oxyalkylated quaternary ammonium compounds are least phytotoxic, produce marked growth regulating effects on a broad species of plants and are not easily decomposed by microorganisms.

2 Claims, No Drawings

OXYALKYLATED QUATERNARY AMMONIUM COMPOUNDS AND PLANT GROWTH REGULATING COMPOSITIONS CONTAINING SAID COMPOUNDS

BACKGROUND OF THE INVENTION

The present invention relates to novel oxyalkylated quaternary ammonium compounds, processes for production thereof and plant growth regulating compositions containing said compounds.

A large number of chemicals are known to regulate or modulate growth of plants but most of such agrochemicals heretofore available are either injurious to crop plants or effective for only limited varieties of plants.

Furthermore, even if they do little harm to plants, many chemicals are so readily decomposed by microorganisms that they cannot exhibit a sufficient regulating effect on plant growth under field conditions (Japanese Kokai Patent Publication No. 61-24501, No. 61-91104, No. 61-91105, No. 61-91106, No. 62-26205, and No. 62-294603).

SUMMARY OF THE INVENTION

It is an object of the present invention to provide a novel oxyalkylated quaternary ammonium compound which is least phytotoxic, exerts a potent plant growth regulating action on a broad species of plants and is not easily decomposed by microorganisms.

It is another object to provide processes for production of said compound.

It is a still another object to provide a plant growth regulating composition containing said compound as an active ingredient.

The novel oxyalkylated quaternary ammonium compound of the present invention consists of a cationic group of the general formula

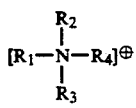  (1)

wherein $R_1$ means an $C_{6-22}$ alkyl or alkenyl group, $R_2$ means a $C_{1-4}$ alkyl or hydroxyalkyl group and $R_3$ and $R_4$ independently mean $(BO)_xH$ where B is a $C_{1-4}$ alkylene group and x means a whole or fractional number of 1 to 5 and an anionic group selected from the class consisting of carboxylic acid residues, aminosulfonic acid residues and phosphate ester residues.

The processes for producing said oxyalkylated quaternary ammonium compound in accordance with the invention generally comprise reacting a quaternary ammonium compound of the general formula

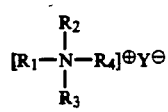  (2)

wherein $R_1$, $R_2$, $R_3$ and $R_4$ are respectively as defined above and Y means Cl, Br, I or F with at least one member of the class consisting of alkali metal salts of carboxylic acids, alkaline earth metal salts of carboxylic acids, alkali metal salts of aminosulfonic acids, alkaline earth metal salts of aminosulfonic acids, alkali metal salts of phosphoric acid esters and alkaline earth metal salts of phosphoric acid esters in a solvent, either in the presence of a small amount of said novel oxyalkylated quaternary ammonium compound or in the absence thereof. The solvent mentioned just above is preferably selected from the class consisting of straight-chain or branched $C_{1-6}$ alcohols, methyl ethyl ketone, dimethyl sulfoxide, dimethylformamide, dimethylacetamide, dioxane, ethyl acetate and cyclohexanol, and these solvents may be used singly or in combination.

The plant growth regulating composition of the present invention contains the above-mentioned novel oxyalkylated quaternary ammonium compound.

DETAILED DESCRIPTION OF THE PREFERRED EMBODIMENTS

The reaction for production of the novel oxyalkylated quaternary ammonium compound is generally conducted at 30° to 100° C. for about 3 to 24 hours.

After completion of the reaction, the byproduced alkali metal halide or alkaline earth metal halide is filtered off and the solvent is removed from the filtrate to isolate the object compound.

If the produced compound is to be further purified, the residue on evaporation of the solvent is dissolved in a solvent, such as a straight-chain or branched $C_{1-6}$ alcohol, acetone, methyl ethyl ketone, n-hexane, cyclohexane, benzene, toluene, xylene or the like or an appropriate mixture of such solvents and the solution is filtered. The filtrate is then concentrated or cooled to recover purified materials.

Preferred examples of the solvent to be used in the production processes of the present invention include, as aforesaid, straight-chain or branched $C_{1-6}$ alcohols, ethyl acetate, dioxane, methyl ethyl ketone, cyclohexanol, dimethyl sulfoxide, dimethylformamide and dimethylacetamide, although other solvents may likewise be employed unless they interfere with the intended reaction. The preferred amount of the solvent is one to 10-fold by weight relative to the combined weight of said compound (2) and said alkali metal salt or alkaline earth metal salt.

It should be understood that the presence of water in the reaction system in a proportion not exceeding about 10 weight percent of the above-mentioned combined weight does not interfere with the reaction.

The reaction can also be conducted in the presence of not more than about 10 weight percent of the novel oxyalkylated quaternary ammonium compound of the invention relative to the above-mentioned combined weight. In such a case or when the compound (2) is the chloride or bromide, an alkali iodide may be added in a proportion of not more than 10 weight percent of compound (2). Furthermore, in order to prevent discoloration of the reaction system, nitrogen gas may be introduced into the reaction system at a low flow rate.

A preferred class of the novel oxyalkylated quaternary ammonium compound according to the present invention can be written as follows.

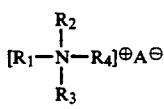  (3)

wherein $R_1$, $R_2$, $R_3$ and $R_4$ are respectively as defined hereinbefore, $A^\ominus$ is $R_5NHR_6COO^\ominus$,

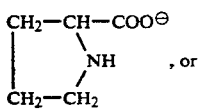, or

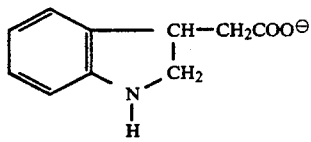

where $R_5$ means a hydrogen atom, an $C_{1-4}$ alkyl group, $CH_2(OH)—$, $CH_2SCH_2CH_2—$,

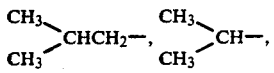

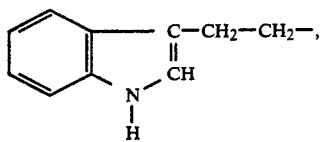

$NH_2CH_2(CH_2)_3—$, or $HSCH_2—$, and $R_6$ means CH, $CH_2$ or an aromatic group.

The process for producing the above compound (3) comprises reacting a quaternary ammonium compound of general formula (2) with a compound of general formula (4)

$$R_5NHR_6COOD \quad (4),$$

a compound of general formula (5)

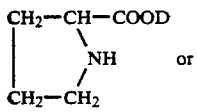

a compound of general formula (6)

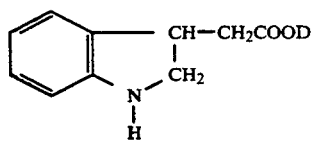

wherein $R_5$ and $R_6$ are as defined hereinbefore and D means an alkali metal atom or an alkaline earth metal atom in a solvent, such as those mentioned hereinbefore, either in the presence of a small amount of the novel oxyalkylated quaternary ammonium compound (3) or in the absence thereof.

Examples of compound (2) include, among others, octylmethyldihydroxyethylammonium chloride, laurylmethyldihydroxyethylammonium bromide, oleylethyldihydroxyethylammonium iodide, stearylmethyldihydroxypropylammonium chloride, hexylethyldihydroxybutylammonium bromide, oleyltrihydroxyethylammonium chloride, lauryltrihydroxyethylammonium chloride, stearyltrihydroxyethylammonium chloride, oleyltrihydroxyethylammonium bromide, octyldihydroxyethylhydroxypropylammonium chloride, oleylmethyldihydroxyethoxyethylammonium chloride and so on.

Examples of the compound of general formula (4), (5), or (6) include alkali metal or alkaline earth metal salts of amino acids such as glycine potassium salt, sarcosine sodium salt, alanine potassium salt, leucine potassium salt, valine sodium salt, cysteine sodium salt, potasssium indoleacetate, potassium pyrrolidonecarboxylate, serine calcium salt, methionine potassium salt, proline potassium salt, tryptophan sodium salt, lysine calcium salt, potassium aminobenzoate and so on.

The preferred ratio of compound (4), (5) or (6) to compound (2) is 1 to 1.5 moles of (4), (5) or (6) to each mole of (2).

An example of the reaction may be written as follows.

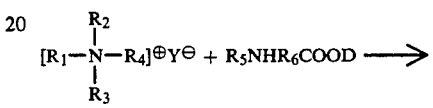

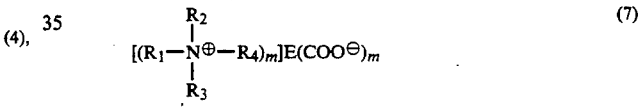

Another preferred class of the novel oxyalkylated quaternary ammonium compound according to the present inevention can be expressed by the general formula

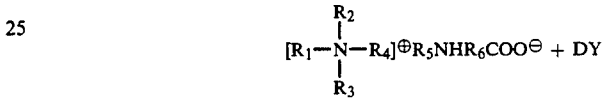
(7)

wherein $R_1$, $R_2$, $R_3$ and $R_4$ are respectively as defined hereinbefore, m means 2 or 3, and E means an $C_{1-10}$ alkyl group, an alkylene group, a hydroxyalkyl group, a sulfur-containing alkyl group, an aminoalkyl group or a sulfur-containing aminoalkyl group or the absence of such a group.

For the production of the above compound (7), said quaternary ammonium compound (2) is reacted with a compound of general formula (8)

$$E(COOD)_m \quad (8)$$

wherein E and m are respectively as defined above and D means an alkali metal atom or an alkaline earth metal atom in a solvent, such as those mentioned hereinbefore, either in the presence of a small amount of the novel oxyalkylated quaternary ammonium compound of general formula (7) or in the absence thereof.

As compound (2) for this reaction, any of the specific compounds (2) mentioned hereinbefore, for instance, can be employed.

Examples of the compound of general formula (8) include potassium maleate, potassium succinate, potassium fumarate, sodium malonate, potassium adipate, potassium malate, potassium citrate, sodium tricarballylate, potassium tartarate, potassium aspartate, potassium thiodipropionate, cystine potassium salt, sodium thiodiglycolate, potassium oxalate, potassium aconitate and so on.

The reaction ratio of compound (2) to compound (8) may be one mole of compound (2) per carboxyl group of compound (8). The ratio may be 1 to 1.2 carboxyl groups of (8) per mole of compound (2).

This reaction can be written as follows.

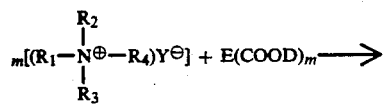 + E(COOD)$_m$ ⟶

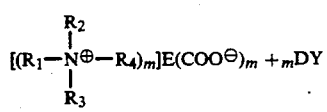

A still another preferred class of the novel oxyalkylated quaternary ammonium compound according to the present invention can be expressed by the following general formula

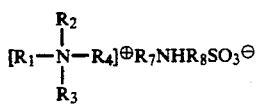 (9)

wherein $R_1$, $R_2$, $R_3$ and $R_4$ are respectively as defined hereinbefore, $R_7$ means a hydrogen atom or an $C_{1-6}$ alkyl group, and $R_8$ means an $C_{1-6}$ alkylene group or an aromatic group.

This class of compound can be produced by reacting a quaternary ammonium compound of general formula (2) with a compound of general formula (10)

$R_7NHR_8SO_3D$ (10)

wherein $R_7$, $R_8$ and D are respectively as defined hereinbefore in a solvent, such as those mentioned hereinbefore, either in the presence of a small amount of the novel oxyalkylated quaternary ammonium compound (9) or in the absence thereof.

As compound (2) for this reaction, any of the specific compounds (2) mentioned hereinbefore, for instance can be employed.

Examples of the compound of general formula (10) include salts of aminoalkylsulfonic acids or aromatic aminosulfonic acids, such as methyltaurine sodium salt, taurine potassium salt, sodium sulfanilate, potassium naphthionate, sodium aminobutanesulfonate, potassium aminomethanesulfonate and so on.

The preferred reaction ratio of compound (10) to compound (2) is 1 to 1.5 moles of (10) to each mole of (2).

This reaction may be written as follows.

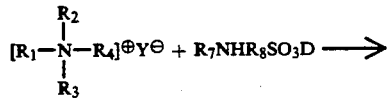 + $R_7NHR_8SO_3D$ ⟶

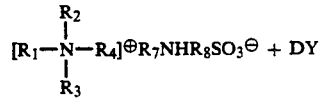 + DY

A still another preferred class of the novel oxyalkylated quaternary ammonium compound according to the present invention can be represented by the following general formula

 (11)

wherein $R_1$, $R_2$, $R_3$ and $R_4$ are respectively as defined hereinbefore and $R_9$ means a hydrogen atom, a saturated or unsaturated $C_{1-22}$ alkyl group, a hydroxyalkyl group, an alkylene group, a mercaptoalkyl group, an aromatic group, an aromatic group-substituted alkyl group, a hydroxy-containing aromatic group, an alkylaryl group,

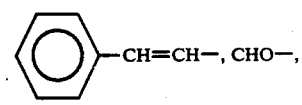

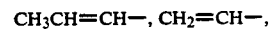

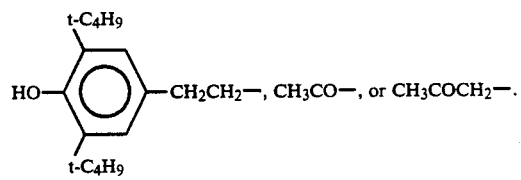

The above compound can be produced by reacting a quaternary ammonium compound of general formula (2) with a compound of general formula (12)

$R_9COOD$ (12)

wherein $R_9$ and D are respectively as defined hereinbefore in a solvent, such as those mentioned hereinbefore, either in the presence of a small amount of the novel oxyalkylated quaternary ammonium compound of general formula (11) or in the absence thereof.

As compound (2) for this reaction, any of the various specific compounds (2) mentioned hereinbefore, for instance, can be employed.

Examples of compound (12) include, among others, potassium acetate, potassium propionate, sodium glycolate, potassium cinnamate, potassium salicylate, sodium acetoacetate, potassium mercaptopropionate, sodium octylate, potassium formate, calcium acrylate, potassium gluconate, sodium benzoate, potassium oleate, sodium octylate, potassium pentadecanate, potassium glycolate, potassium crotonate, sodium sorbate, sodium glyoxalate, sodium phenylacetate, potassium ricinoleate, sodium glyoxalate, potassium coumarinate, potassium gallate, potassium lactate, sodium pyruvate, potassium thioglycolate, potassium 1-hydroxy-2,6-di-t-butylphenyl-4-propionate, potassium toluylate, and so on.

The preferred reaction ratio of compound (12) to compound (2) is 1 to 1.5 moles of (12) to each mole of compound (2).

A still another preferred class of the novel oxyalkylated quaternary ammonium compound according to the present invention can be represented by the following general formula

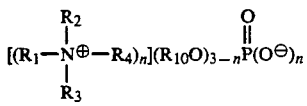 (13)

wherein $R_1$, $R_2$, $R_3$ and $R_4$ are respectively as defined hereinbefore, n means 1 or 2, and $R_{10}$ means a straight-chain or branched $C_{1-22}$ alkyl group, a $C_{1-22}$ alkyl-containing alkoxypolyethoxyethyl group, a $C_{1-22}$ alkyl-containing alkylphenoxypolyethoxyethyl group, or a mono-, di- or tristyrylphenoxypolyethoxyethyl group, and when there are two $R_{10}$'s, they may be the same or different.

The compound of this class can be produced by reacting a quaternary ammonium compound of general formula (2) with a compound of general formula (14)

 (14)

wherein $R_{10}$, D and n are respectively as defined hereinbefore in a solvent, such as those mentioned hereinbefore, either in the presence of a small amount of the novel oxyalkylated quaternary ammonium compound of general formula (13) or in the absence thereof.

As compound (2) for this reaction, any of the various compounds (2) mentioned hereinbefore, for instance, can be employed.

Examples of compound (14) include potassium or sodium salts of isopropyl phosphate, diisopropyl phosphate, mono-/di-isooctyl phosphate (mole ratio 1:1), dilauryl phosphate, phenoxyethyl phosphate, diphenoxyethyl phosphate, nonylphenoxytetraethoxyethyl phosphate, mono-/di-lauryloxydiethoxyethyl phosphate (mole ratio 1:1), styrylphenoxyethoxyethyl phosphate, di(distyrylphenoxy)pentaethoxyethyl phosphate and so on.

The preferred reaction ratio of compound (2) to compound (14) is 1 to 1.5 moles of (2) to each mole of (14) when n in general formula (14) means 1, and 2 to 3 moles of (2) to each mole of (14) when n means 2. It should be understood that a mixture of compound (14) wherein n is 1 and compound (14) wherein n is 2 can be used for this reaction.

In accordance with the production processes of the present invention, the novel oxyalkylated quaternary ammonium compound consisting of a cationic group of general formula (1) and an anionic group selected from the class consisting of carboxylic acid residues, aminosulfonic acid residues and phosphoric acid ester residues can be easily obtained in high yield. The novel oxyalkylated quaternary ammonium compound according to the present invention is least phytotoxic, exhibits a potent growth modulating action on a broad spectrum of plants and is resistant to the attack of microorganisms. Therefore, the plant growth modulating composition of the present invention is very useful.

For use as a plant growth modulator, the oxyalkylated ammonium compound of the invention can be used in the per se known ways. For example, the seeds of plant whose growth is to be regulated may be immersed in an aqueous solution of the compound before sowing. Although the optimum concentration of the solution and the immersion time vary with different plants, the concentration may range from 0.0001 to 0.1%, for instance, and the immersion time may range from several hours to tens of hours.

The following examples are merely intended to illustrate the invention in further detail and should by no means be construed as defining the scope of the invention.

EXAMPLE 1

A four-necked flask fitted with stirrer and condenser means was charged with 40.5 g of oleylmethyldihydroxyethylammonium chloride, 13 g of potassium glycinate and 200 g of isobutyl alcohol and the reaction was conducted at 40°–50° C. in an atmosphere of nitrogen gas introduced at a low flow rate for 6 hours. The precipitate was then collected by filtration and washed with 30 ml of isobutyl alcohol. The filtrate and the washings were combined and concentrated under reduced pressure. The residue was dissolved in 200 g of toluene and filtered. The filtrate was then concentrated to give 43.1 g (theoretical yield 44.4 g) of oleylmethyldihydroxyethylammonium glycinate as a waxy product. The elemental analysis and infrared absorption data are given below.

Analysis (%; calcd. in parentheses)
C, 67.05 (67.56)
H, 11.75 (11.71)
O, 14.18 (14.41)
N, 6.21 ( 6.30)
Cl, 0.01
IR In addition to the absorptions of oleylmethyldihydroxyethylammonium, absorptions assignable to $-COO^{\ominus}$ of glycine were observed at 1600 cm$^{-1}$ and 1380 cm$^{-1}$.

EXAMPLE 2

A four-necked flask fitted with stirrer and condenser means was charged with 37.8 g of laurylmethyldihydroxyethylammonium bromide, 13.9 g of valine sodium salt, 3 g of laurylmethyldihydroxyethylammonium salt of valine and 200 g of isopropyl alcohol and the reaction was conducted at 50° C. in an atmosphere of nitrogen gas introduced at a low flow rate for 4 hours. The precipitate was then collected by filtration and washed with 30 ml of isopropyl alcohol. The filtrate and washings were combined and the isopropyl alcohol was distilled off under reduced pressure. The residue was then dissolved in 200 g of benzene and the insolubles were filtered off. Finally, the benzene was distilled off to give 39.3 g (theoretical yield 41.4 g) of laurylmethyldihydroxyethylammonium salt of valine as a waxy product.

Analysis (%; calcd. in parentheses)
C, 63.58 (63.76)
H, 11.53 (11.59)
O, 15.40 (15.45)
N, 6.71 ( 6.76)
Br, 0.02

EXAMPLE 3

A four-necked flask fitted with stirrer and condenser means was charged with 32.5 g of decyltrihydroxyethylammonium chloride, 200 g of isopropyl alcohol, 25.6 g of tryptophan potassium salt and 3 g of potassium iodide and the reaction was conducted at 60° C. for 8 hours. The reaction mixture was then allowed to stand overnight and the precipitate was collected by filtration and washed with 200 g of isopropyl alcohol. The filtrate and the washings were combined and concentrated. The residue was dissolved in 200 g of toluene and the insolubles were filtered off. Finally, the filtrate was concentrated to give 45.6 g (theoretical yield 48.1 g) of decyltrihydroxyethylammonium salt of tryptophan as a waxy product.

Analysis (%; cald. in parentheses)
C, 63.98 (64.86)
H, 9.79 ( 9.77)
N, 8.68 ( 8.73)
O, 16.51 (16.63)
Cl, 0.02

EXAMPLE 4

The compound synthesized in Example 1 was dissolved in water to prepare 0.0001%, 0.001%, 0.01% and 0.1% aqueous solutions and soybean, corn and paddy rice seeds were immersed in the solutions at 25±2° C. for 12 hours. Then, polyethylene cups were filled with vermiculite and the above seeds were sown. The cups were placed in a green house maintained at an interior temperature of 25° C. and kept for 10 days, with daily replenishment of water. As controls, the corresponding seeds soaked in water were similarly grown.

Tables 1 and 3 show the mean stem length and leaves number and mean root length of each plant. It is apparent from the data that the compound according to Example 1 has plant growth regulating activity.

TABLE 1

Effects on the stem length and leaves number and root length of the soybean plant

| | Control | Compound of the invention (Example 1) | | | |
|---|---|---|---|---|---|
| | Untreated | 0.0001% | 0.001% | 0.01% | 0.1% |
| Stem length, cm | 18 | 18.5 | 19.3 | 21.0 | 19.1 |
| Number of leaves | 7.5 | 7.8 | 8.3 | 8.7 | 7.9 |
| Root length, cm | 11 | 11.3 | 11.2 | 12.5 | 11.5 |

TABLE 2

Effects on the stem length and leaves number and root length of the corn plant

| | Control | Compound of the invention (Example 1) | | | |
|---|---|---|---|---|---|
| | Untreated | 0.0001% | 0.001% | 0.01% | 0.1% |
| Stem length, cm | 12 | 16.2 | 15.8 | 15.0 | 15.0 |
| Number of leaves | 2.6 | 3.0 | 3.2 | 3 | 2.8 |
| Root length, cm | 16.8 | 18.4 | 17.6 | 23.2 | 17.8 |

TABLE 3

Effects on the stem length and leaves number and root length of the rice plant

| | Control | Compound of the invention (Example 1) | | | |
|---|---|---|---|---|---|
| | Untreated | 0.0001% | 0.001% | 0.01% | 0.1% |
| Stem length, cm | 7.4 | 11.8 | 13.0 | 12.2 | 9.6 |
| Number of leaves | 1.6 | 2 | 2 | 2 | 2 |
| Root length, cm | 11.0 | 12.8 | 14.2 | 12.6 | 11.6 |

EXAMPLE 5

A four-necked flask fitted with stirrer and condenser means was charged with 81 g of oleylmethyldihydroxyethylammonium chloride, 20 g of potassium succinate and 200 g of isobutyl alcohol and the reaction was conducted at 40°-50° C. in an atmosphere of nitrogen gas introduced at a low flow rate for 6 hours. The precipitate was then collected by filtration and washed with 30 ml of isobutyl alcohol, and the filtrate and washings were combined and concentrated under reduced pressure. The residue was dissolved in 200 g of toluene and filtered and the filtrate was concentrated to give 82 g (theoretical yield 85.6 g) of di(oleylmethyldihydroxyethylammonium) succinate as a waxy product. The element analysis and IR data are shown below.

Analysis (%; calcd. in parentheses)
C, 70.65 (70.09)
H, 11.61 (11.68)
O, 14.89 (14.95)
N, 3.32 (3.27)
Cl, 0.01
IR In addition to the absorptions of oleylmethyldihydroxyethylammonium, absorptions assignable to —COO$^\ominus$ of the succinate were found at 1570 cm$^{-1}$ and 1380 cm$^{-1}$.

EXAMPLE 6

A four-necked flask fitted with stirrer and condenser means was charged with 73.6 g of laurylmethyldihydroxyethylammonium bromide, 19.0 g of sodium aspartate, 200 g of isopropyl alcohol and 3.5 g of di(laurylmethyldihydroxyethylammonium) aspartate and the reaction was conducted at 50° C. in an atmosphere of nitrogen gas introduced at a low flow rate for 4 hours. The precipitate was then collected by filtration and washed with 30 ml of isopropyl alcohol. The filtrate and washings were combined and the isopropyl alcohol was distilled off under reduced pressure. The residue was dissolved in toluene and the insolubles were filtered off. Finally, the toluene was distilled off under reduced pressure to give 65.7 g (theoretical yield 70.7 g) of di(-laurylmethyldihydroxyethylammonium) aspartate as a waxy product.

Analysis (%; calcd. in parentheses)
C, 64.53 (64.49)
H, 11.40 (11.45)
O, 17.98 (18.10)
N, 5.91 (5.94)
Br, 0.008

EXAMPLE 7

A four-necked flask fitted with stirrer and condenser means was charged with 81 g of oleylmethyldihydroxyethylammonium chloride, 33 g of cystine potassium salt and 200 g of isopropyl alcohol and the reaction was conducted at 65°-75° C. in an atmosphere of nitrogen gas introduced at a low flow rate for 7 hours. The precipitate was then filtered off and the filtrate was concentrated under reduced pressure. The residue was dissolved in 200 g of toluene and the insolubles were filtered off. Finally, the filtrate was concentrated to give 95.2 g (theoretical yield 97.8 g) of di(oleylmethyldihydroxyethylammonium) cystinate as a waxy product.

Analysis (%; calcd. in parentheses)
C, 63.72 (63.80)
H, 10.78 (10.83)
O, 13.01 (13.08)
N, 5.66 (5.72)
S, 6.52 (6.54)
Cl, 0.008

EXAMPLE 8

A four-necked flask fitted with stirrer and condenser means was charged with 87.1 g of oleyltrihydroxyethylammonium chloride, 21 g of sodium tartarate and 200 g of isobutyl alcohol and the reaction was conducted at 80°–90° C. for 7 hours. The precipitate was then filtered off and the filtrate was concentrated under reduced pressure. The residue was dissolved in 200 g of acetone and the insolubles were filtered off. Finally, the filtrate was concentrated to give 90 g (theoretical yield 94.8 g) of di(oleyltrihydroxyethylammonium) tartarate as a waxy product.

Analysis (%; calcd. in parentheses)
C, 65.79 (65.82)
H, 10.93 (10.97)
O, 20.21 (20.25)
N, 2.89 (2.95)
Cl, 0.1

EXAMPLE 9

The compound synthesized in Example 5 was dissolved in water to prepare 0.0001%, 0.001%, 0.01% and 0.1% aqueous solutions and soybean, corn and paddy rice seeds were immersed in the solutions at 25° C. for 12 hours. Then, polyethylene cups were filled with vermiculite and the above seeds were sown. The cups were placed in a green house maintained at an interior temperature 25° C. and kept for 10 days, with daily replenishment of water. As controls, the corresponding seeds soaked in water were similarly grown.

Tables 4 to 6 show the mean stem length and leaves number and mean root length of each plant. It is apparent from the data that the compound according to Example 5 has plant growth regulating activity for dicotyledons and monocotyledons.

TABLE 4

Effects on the stem length and leaves number and root length of the soybean plant

|  | Control | Compound of the invention (Example 5) | | | |
|---|---|---|---|---|---|
|  | Untreated | 0.0001% | 0.001% | 0.01% | 0.1% |
| Stem length, cm | 18 | 25.0 | 23.0 | 23.0 | 18.5 |
| Number of leaves | 7.5 | 10.3 | 9.2 | 8.3 | 7.9 |
| Root length, cm | 11.0 | 14.2 | 13.5 | 12.6 | 11.5 |

TABLE 5

Effects on the stem length and leaves number and root length of the corn plant

|  | Control | Compound of the invention (Example 5) | | | |
|---|---|---|---|---|---|
|  | Untreated | 0.0001% | 0.001% | 0.01% | 0.1% |
| Stem length, cm | 12 | 12.1 | 16.6 | 15.6 | 13.6 |
| Number of leaves | 2.6 | 3 | 3 | 3 | 2.8 |
| Root length, cm | 16.8 | 17.0 | 23.4 | 21.4 | 17.4 |

TABLE 6

Effects on the stem length and leaves number and root length of the rice plant

|  | Control | Compound of the invention (Example 5) | | | |
|---|---|---|---|---|---|
|  | Untreated | 0.0001% | 0.001% | 0.01% | 0.1% |
| Stem length, cm | 7.4 | 12.2 | 14.6 | 13.9 | 12.3 |
| Number of leaves | 1.6 | 2 | 2.3 | 2.0 | 2 |
| Root length, cm | 11.0 | 15.4 | 13.6 | 13.2 | 13 |

EXAMPLE 10

A four-necked flask fitted with stirrer and condenser means was charged with 39 g of oleylmethyldihydroxyethylammonium chloride, 18 g of methyltaurine sodium salt and 200 g of isopropyl alcohol and the reaction was conducted at 40°–50° C. in an atmosphere of nitrogen gas introduced at a low flow rate for 6 hours. The precipitate was then collected by filtration and washed with 30 ml of isobutyl alcohol. The filtrate and the washings were combined and concentrated under reduced pressure. The residue was dissolved in 200 g of toluene and filtered. The filtrate was then concentrated to give 46.3 g (theoretical yield 49.2 g) of oleylmethyldihydroxyethylammonium methyltaurate as a waxy product. The elemental analysis and infrared absorption data are given below.

Analysis (%; calcd. in parentheses)
C, 60.53 (60.91)
H, 11.31 (11.37)
O, 16.09 (16.24)
N, 5.58 (5.68)
S, 6.46 (6.49)
Cl, 0.01

IR

In addition to the absorptions of oleylmethyldihydroxyethylammonium, absorptions assignable to $SO_3$ of methyltaurine were observed at 1200 cm$^{-1}$, 1030 cm$^{-1}$, 610 cm$^{-1}$ and 520 cm$^{-1}$.

EXAMPLE 11

A four-necked flask fitted with stirrer and condenser means was charged with 39 g of oleylmethyldihydroxyethylammonium chloride, 23 g of potassium sulfanilate and 200 g of isopropyl alcohol and the reaction was conducted at 40°–50° C. in an atmosphere of nitrogen gas introduced at a low flow rate for 6 hours. The precipitate was then collected by filtration and washed with 30 ml of isobutyl alcohol. The filtrate and the washings were combined and concentrated under reduced pressure. The residue was dissolved in 200 g of toluene and filtered. The filtrate was then concentrated to give 49.8 g (theoretical yield 54.9 g) of oleylmethyldihydroxyethylammonium sulfanilate as a waxy product. The elemental analysis is shown below.

Analysis (%; calcd. in parentheses)
C, 63.90 (64.20)
H, 9.85 (9.96)
O, 5.10 (5.16)
N, 14.55 (14.76)
S, 5.89 (5.90)

EXAMPLE 12

A four-necked flask fitted with stirrer and condenser means was charged with 39.8 g of lauryltrihydroxyethylammonium bromide, 15.9 g of sodium aminomethanesulfonate and 200 g of isopropyl alcohol and the reaction was conducted at 70°-80° C. in an atmosphere of nitrogen gas introduced at a low flow rate for 5 hours. The precipitate was then filtered off and the filtrate was concentrated. The residue was dissolved in 200 g of isopropyl alcohol and the insolubles were filtered off. Finally, the filtrate was concentrated to give 40.1 g (theoretical yield 42.8 g) of lauryltrihydroxyethylammonium aminomethanesulfonate as a waxy product. The elemental analysis is shown below.

Analysis (%; calcd. in parentheses)
C, 55.52 (55.60)
N, 6.44 (6.54)
H, 10.31 (10.28)
O, 22.29 (22.43)
S, 7.51 (7.47)

EXAMPLE 13

The compound synthesized in Example 10 is dissolved in water to prepare 0.0001%, 0.001%, 0.01% and 0.1% aqueous solutions and soybean, corn and paddy rice seeds were immersed in the solutions at 25° C. for 12 hours. Then, polyethylene cups were filled with vermiculite and the above seeds were sown. The cups are placed in a green house maintained at an interior temperature of 25° C. and kept for 10 days. As controls, the corresponding seeds soaked in water are similarly grown.

Tables 7 to 9 show the predicted mean stem length and leaves number and mean root length of each test plant.

It is apparent that the compound of Example 10 has plant growth regulating activity.

TABLE 7

Effects on the stem length and leaves number and root length of the soybean plant

| | Control | Compound of the invention (Example 10) | | | |
|---|---|---|---|---|---|
| | Untreated | 0.0001% | 0.001% | 0.01% | 0.1% |
| Stem length, cm | 18 | 22.6 | 23.0 | 20.4 | 19.0 |
| Number of leaves | 7.5 | 8.0 | 8.9 | 8.7 | 8.5 |
| Root length, cm | 11.0 | 13.1 | 14.2 | 16.6 | 11.2 |

TABLE 8

Effects on the stem length and leaves number and root length of the corn plant

| | Control | Compound of the invention (Example 10) | | | |
|---|---|---|---|---|---|
| | Untreated | 0.0001% | 0.001% | 0.01% | 0.1% |
| Stem length, cm | 12 | 22.1 | 24.8 | 23.6 | 22.2 |
| Number of leaves | 2.6 | 3.3 | 3.6 | 3.0 | 2.8 |
| Root length, cm | 16.8 | 21.2 | 22.3 | 19.2 | 17.7 |

TABLE 9

Effects on the stem length and leaves number and root length of the rice plant

| | Control | Compound of the invention (Example 10) | | | |
|---|---|---|---|---|---|
| | Untreated | 0.0001% | 0.001% | 0.01% | 0.1% |
| Stem length, cm | 7.4 | 8.9 | 10.1 | 9.5 | 8.3 |
| Number of leaves | 1.6 | 2.0 | 2.4 | 2.5 | 2.0 |
| Root length, cm | 11.0 | 13.5 | 17.5 | 15.3 | 14.8 |

EXAMPLE 14

A four-necked flask fitted with stirrer and condenser means was charged with 40.5 g of oleylmethyldihydroxyethylammonium chloride, 12.0 g of potassium glycolate and 200 g of isobutyl alcohol and the reaction was conducted at 80°-85° C. in an atmosphere of nitrogen gas introduced at a low flow rate for 7 hours. The precipitate was then collected by filtration and washed with 30 ml of isobutyl alcohol. The filtrate and the washings were combined and concentrated under reduced pressure. The residue was dissolved in 200 g of toluene and filtered. The filtrate was then concentrated to give 41.0 g (theoretical yield 44.3 g) of oleylmethyldihydroxyethylammonium glycolate as a waxy product. The elemental analysis and infrared absorption data are given below.

Analysis (%; calcd. in parentheses)
C, 67.10 (67.72)
H, 10.89 (11.06)
O, 18.20 (18.06)
N, 3.03 (3.16)
Cl, 0.1

IR

In addition to the absorptions of oleylmethyldihydroxyethylammonium, absorptions assignable to —COO$^\ominus$ of glycolic acid were observed at 1580 cm$^{-1}$ and 1385 cm$^{-1}$.

EXAMPLE 15

A four-necked flask fitted with stirrer and condenser means was charged with 40.5 g of oleylmethyldihydroxyethylammonium chloride, 10 g of potassium formate and 150 g of isopropyl alcohol and the reaction was conducted at 75°-80° C. in an atmosphere of nitrogen gas introduced at a low flow rate for 8 hours. The precipitate was then collected by filtration and washed with 50 ml of isopropyl alcohol. The filtrate and the washings were combined and concentrated under reduced pressure. The residue was dissolved in 200 g of benzene and filtered. Finally, the filtrate was concentrated to give 39.3 g (theoretical yield 41.3 g) of oleylmethyldihydroxyethylammonium formate as a waxy product. The elemental analysis and infrared absorption data are given below.

Analysis (%; calcd. in parentheses)
C, 69.21 (69.73)
H, 11.43 (11.38)
O, 15.11 (15.49)
N, 3.29 (3.38)
Cl, 0.05

IR

In addition to the absorptions of oleylmethyldihydroxyethylammonium, absorptions assignable to —COO$^\ominus$ of formic acid were observed at 1590 cm$^{-1}$ and 1380 cm$^{-1}$.

EXAMPLE 16

A four-necked flask fitted with stirrer and condenser means was charged with 43.3 g of oleyltrihydroxyethylammonium chloride, 20 g of sodium cinnamate and 200 g of isobutyl alcohol and the reaction was conducted at 40°-50° C. in an atmosphere of nitrogen gas introduced at a low flow rate for 6 hours. The precipitate was then collected by filtration and washed with 30 ml of isobutyl alcohol. The filtrate and the washings were combined and concentrated under reduced pressure and the residue was dissolved in 200 g of toluene and filtered. Finally, the filtrate was concentrated to give 50.9 g (theoretical yield 54.5 g) of oleyltrihydroxyethylammonium cinnamate as a waxy product. The elemental analysis is shown below.

Analysis (%; calcd. in parentheses)
C, 72.63 (72.59)
H, 9.97 (10.08)
O, 14.51 (14.66)
N, 2.58 (2.56)
Cl, 0.07

EXAMPLE 17

The compound synthesized in Example 15 is dissolved in water to prepare 0.0001%, 0.001%, 0.01% and 0.1% aqueous solutions and soybean, corn and paddy rice seeds are immersed in the solutions at 25° C. for 12 hours. Then, polyethylene cups are filled with vermiculite and the above seeds are sown. The cups are placed in a green house maintained at an interior temperature of 25° C. and kept for 10 days, with daily replenishment of water. As controls, the corresponding seeds soaked in water are similarly grown.

Tables 10 to 12 show the predicted mean stem length and leaves number, mean root length, and germination rate of each plant. As inferred from Table 10, the compound of Example 15 is expected to inhibit the germination of soybean seeds at all concentrations. As to the corn, the compound is expected to inhibit germination over the concentration range of 0.001 to 0.1% as will be seen from Table 11. Regarding the rice plant, as shown in Table 12, the compound is expected to suppress growth at all concentrations.

TABLE 10

Effects on the stem length and leaves number and root length of the soybean plant

| | Control | Compound of the invention (Example 15) | | | |
|---|---|---|---|---|---|
| | Untreated | 0.0001% | 0.001% | 0.01% | 0.1% |
| Stem length, cm | 18 | 9.6 | 5.3 | 5.1 | 5.0 |
| Number of leaves | 7.5 | 2.5 | 5.0 | 3.3 | 3.3 |
| Root length, cm | 11.0 | 3.5 | 3.3 | 8.0 | 6.0 |
| Germination rate, % | 100 | 30 | 30 | 10 | 10 |

TABLE 11

Effects on the stem length and leaves number and root length of the corn plant

| | Control | Compound of the invention (Example 15) | | | |
|---|---|---|---|---|---|
| | Untreated | 0.0001% | 0.001% | 0.01% | 0.1% |
| Stem length, cm | 12 | 15.3 | 8.0 | 9.8 | 12.5 |
| Number of leaves | 2.6 | 2.6 | 2.4 | 2.4 | 2.8 |
| Root length, cm | 16.8 | 19.3 | 4.5 | 4.5 | 14.7 |
| Germination rate, % | 100 | 100 | 50 | 50 | 10 |

TABLE 12

Effects on the stem length and leaves number and root length of the rice plant

| | Control | Compound of the invention (Example 15) | | | |
|---|---|---|---|---|---|
| | Untreated | 0.0001% | 0.001% | 0.01% | 0.1% |
| Stem length, cm | 7.4 | 6.5 | 7.3 | 6.6 | 9.3 |
| Number of leaves | 1.6 | 1.5 | 1.5 | 1.8 | 1.5 |
| Root length, cm | 11.0 | 12.0 | 12.4 | 7.5 | 6.1 |

EXAMPLE 18

A four-necked flask fitted with stirrer and condenser means was charged with 40.5 g of oleylmethyldihydroxyethylammonium chloride, 14.2 g of an equimolar mixture of potassium diisopropyl phosphate and potassium monoisopropyl phosphate and 200 g of isopropyl alcohol and the reaction was conducted at 70°-80° C. in an atmosphere of nitrogen gas introduced at a low flow rate for 7 hours. The precipitate was then collected by filtration and washed with 30 ml of isobutyl alcohol. The filtrate and the washings were combined and concentrated under reduced pressure and the residue was dissolved in 200 g of toluene and filtered. Finally, the filtrate was concentrated to give 47.05 g (theoretical yield 49.09 g) of oleylmethyldihydroxyethylammonium mono/diisopropyl phosphate as a waxy product. The elemental analysis and infrared absorption data are given below.

Analysis (%; calcd. in parentheses)
C, 65.18 (65.50)
H, 11.40 (11.54)
O, 15.60 (15.67)
N, 2.95 (2.93)
P, 4.27 (4.33)
Cl, 0.01

IR

In addition to the absorptions of oleylmethyldihydroxyethylammonium, absorptions assignable to —PO=O and ROP— were observed at 1220 cm$^{-1}$ and 1065 cm$^{-1}$.

EXAMPLE 19

A four-necked flask fitted with stirrer and condenser means was charged with 40.5 g of oleylmethyldihydroxyethylammonium chloride, 21.5 g of potassium monolaurylethoxyethyl phosphate prepared from lauryl alcohol-ethylene oxide (2 mol) adduct and 150 g of isopropyl alcohol and the reaction was conducted at 75°-80° C. in an atmosphere of nitrogen gas introduced at a low flow rate for 8 hours. The precipitate was then collected by filtration and washed with 50 ml of isopropyl alcohol. The filtrate and the washings were combined and concentrated under reduced pressure and the residue was dissolved in 200 g of benzene and filtered. The filtrate was then concentrated to give 51.27 g (theoretical yield 54.55 g) of oleylmethyldihydroxyethylammonium laurylethoxyethyl phosphate as a waxy product. The elemental analysis is shown below.

Analysis (%; calcd. in parentheses)

C, 68.01 (68.13)
H, 11.78 (11.81)
O, 14.67 (14.65)
N, 2.58 (2.56)
P, 2.80 (2.83)
Cl, 0.01

EXAMPLE 20

The compound synthesized in Example 18 is dissolved in water to prepare 0.0001%, 0.001%, 0.01% and 0.1% aqueous solutions and soybean, corn and paddy rice seeds are immersed in the solutions at 25° C. for 12 hours. Then, polyethylene cups are filled with vermiculite and the above seeds are sown. The cups are placed in a green house maintained at an interior temperature of 25° C. and kept for 10 days, with daily replenishment of water. As controls, the corresponding seeds soaked in water are similarly grown.

Tables 13 to 15 shown the predicted mean stem length and leaves number and mean root length of each plant.

It is apparent that the compound according to Example 18 has plant growth regulating activity.

TABLE 13

| Effects on the stem length and leaves number and root length of the soybean plant | | | | | |
|---|---|---|---|---|---|
| | Control | Compound of the invention (Example 18) | | | |
| | Untreated | 0.0001% | 0.001% | 0.01% | 0.1% |
| Stem length, cm | 18 | 22.7 | 23.9 | 23.0 | 22.7 |
| Number of leaves | 7.5 | 8.3 | 9.3 | 11.3 | 7.9 |
| Root length, cm | 11.0 | 12.0 | 12.1 | 11.6 | 11.1 |

TABLE 14

| Effects on the stem length and leaves number and root length of the corn plant | | | | | |
|---|---|---|---|---|---|
| | Control | Compound of the invention (Example 18) | | | |
| | Untreated | 0.0001% | 0.001% | 0.01% | 0.1% |
| Stem length, cm | 12 | 15.9 | 16.9 | 17.6 | 15.6 |
| Number of leaves | 2.6 | 2.9 | 3.1 | 2.6 | 3.1 |
| Root length, cm | 16.8 | 18.0 | 21.0 | 20.6 | 19.5 |

TABLE 15

| Effects on the stem length and leaves number and root length of the rice plant | | | | | |
|---|---|---|---|---|---|
| | Control | Compound of the invention (Example 18) | | | |
| | Untreated | 0.0001% | 0.001% | 0.01% | 0.1% |
| Stem length, cm | 7.4 | 9.5 | 10.2 | 8.9 | 10.2 |
| Number of leaves | 1.6 | 2.4 | 2.6 | 2.2 | 2.4 |
| Root length, cm | 11.0 | 12.9 | 14.4 | 12.1 | 13.0 |

What is claimed is:

1. Method of regulating plant growth comprising prior to sowing seeds of the plant, immersing the seeds in a solution of an oxyalkylated quaternary ammonium compound consisting of a cationic group of the following general formula and an anionic group selected from the class consisting of carboxylic acid residues, aminosulfonic acid residues and phosphoric acid ester residues

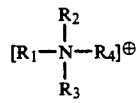

wherein $R_1$ means a $C_{6-22}$ alkyl or alkenyl group, $R_2$ means a $C_{1-4}$ alkyl or hydroxyalkyl group and $R_3$ and $R_4$ independently mean $(BO)_xH$ where B is a $C_{1-4}$ alkylene group and x means a whole or fractional number of 1 to 5.

2. Method according to claim 1 in which the solution is aqueous.

* * * * *